United States Patent [19]

Bargenda

[11] 4,141,248

[45] Feb. 27, 1979

[54] ERGOMETERS

[75] Inventor: Siegfried Bargenda, Rockenhausen, Fed. Rep. of Germany

[73] Assignee: Keiper Trainingsysteme GmbH & Co., Rockenhausen, Fed. Rep. of Germany

[21] Appl. No.: 810,850

[22] Filed: Jun. 28, 1977

[30] Foreign Application Priority Data

Jul. 1, 1976 [DE] Fed. Rep. of Germany ...... 2629516

[51] Int. Cl.² ............................................. G01L 5/02
[52] U.S. Cl. ................................................... 73/379
[58] Field of Search ................. 73/379; 272/DIG. 6, 272/73, 129, 69; 128/2 S

[56] References Cited

U.S. PATENT DOCUMENTS

| 3,505,992 | 4/1970 | Jaeger | 272/73 R |
|---|---|---|---|
| 3,744,480 | 7/1973 | Gause et al. | 73/379 |
| 3,859,840 | 1/1975 | Gause | 73/379 |

Primary Examiner—Anthony V. Ciarlante
Attorney, Agent, or Firm—Wigman & Cohen

[57] ABSTRACT

An improved ergometer having a driving machine for producing a rotational movement and set in motion by the user is disclosed. The ergometer includes a load device comprising a generator connected to the driving machine, a load connected to the generator output and a regulator which controls the electrical power dissipation of the load device based on a comparison between an actual value produced by an actual value transmitter and a given nominal value produced by a nominal value transmitter. The actual value transmitter comprises two measurement transducers the outputs of which are connected to the inputs of a multiplier. A first transducer, which is in the form of a wire strain gauge attached to an elastically deformable element of the driving machine, such as a foot pedal, measures the torque exerted by the user on the foot pedal and produces an output signal representing the measured torque. The second transducer comprises a tachometer which measures the rotational speed of the driving machine upon which the user applies a torque and produces an output signal representing the measured speed. The output of the multiplier thus represents the power transmitted to the driving machine by the user without the need to proportion the power dissipation between electrical and mechanical power losses.

11 Claims, 2 Drawing Figures

ERGOMETERS

BACKGROUND OF THE INVENTION

The present invention relates to an ergometer having a driving machinery set in motion by the user and producing a rotational movement, a load device consisting of a generator connected with the driving machinery, and a load connected to the generator output, as well as a regulator controlling the electrical power dissipation of the load device on the basis of a comparison between a given nominal value and an actual value produced by an actual value transmitter.

Since the power to be produced by the user of the ergometer on the driving machinery is composed of the electrical power dissipation of the load device and the mechanical losses in the ergometer, the mechanical losses being dependent on the rotational speed, which losses can attain a considerable magnitude, the nominal value transmitted to the regulator in the case of a known ergometer, for example, that disclosed in West German Pat. No. (DT-OS) 1,616,895, is composed of a constant voltage being produced by way of a circuit connected to the generator, and a voltage proportional to the speed of the generator, which voltage is produced by a tachometric device. Nevertheless, the power to be produced by the test person is not independent of the speed since the mechanical losses will only in part increase linearly with the speed. Other components or losses are quadratically dependent on the rotational speed, or increase with the third power, for instance, as in the case for the driving power of a fan for the generator. Therefore, the user cannot produce an exactly defined capacity although the load device is controlled.

SUMMARY AND OBJECTS OF THE INVENTION

The basic proposition of this invention is to provide an ergometer for which the regulator can maintain, at a constant value, the power produced by the user with the driving machinery even at varying driving speeds, while the expenses for the power regulation are kept at a low level. This object is accomplished for the invented ergometer mentioned above by the fact that the actual value transmitter includes a first measurement transducer which determines the torque developed by the user on the driving machinery and transforms the developed torque into a respective electrical signal, a second measurement transducer which determines the speed of the component upon which the measured torque acts and transforms the speed into a respective electrical signal, as well as a multiplier device which determines from these two electrical signals the actual value of the power transmitted by the user to the driving machinery. By reason of the fact, that, for the actual value determination, the input power, i.e., the driving power transmitted by the user to the ergometer, is determined, it becomes irrelevant that the total power loss is composed of an electrical and mechanical power loss and that the latter consists of components having different dependencies on the speed. Therefore, the determination or assumption of the functional relationship between the individual components of the mechanical losses and the speed is eliminated, whereby taking into consideration of the mechanical losses is not only simplified, but also can be accomplished with greater precision. A further important advantage consists of the fact that the mechanical losses of the ergometer are taken into consideration in the actual value, whereby the nominal value can be given as a constant value independent of the speed and the setting of the nominal value is considerably simplified. The regulator can operate analogously or digitally, in the latter case, even by using a microprocessor.

Particularly, when it is to be assumed that the user does not exert a constant torque on the driving machinery as would generally be the case when the driving machinery is provided with foot pedals, it is advantageous to place an integrator between the first measurement transducer and the multiplier unit. The integrator will then form the mean value of the torque during one rotation which is advantageous with regard to the control of the load device.

The torque transmitted by the user to the driving machinery can be measured in different ways. A measurement, for instance, is possible on a coupling. Preferably, the measurement would be effected on an elastically deformable element, particularly, deflecting or deforming in accordance with the torque, by means of a wire strain gauge. It is advantageous to select a rigid structural element. Since, generally, the driving machinery is equipped with a foot pedal, it would also be possible to determine the torque on the basis of the stress of the arms of the foot pedal. For this purpose, a wire strain gauge is also suitable when attached to the arm of the foot pedal. Because of a high sensitivity and an exactitude of measurement, it is advantageous when using a wire strain gauge to provide a wire strain gauge bridge, the output of which is connected to a sum-and-difference amplifier.

Since the nominal value is not subject to any correction, etc., the nominal value transmitter can be constructed in a simple manner. However, the nominal value could, for example, also be given by means of a processor and the nominal value transmitter could then comprise a digital-to-analog converter connected to the output of the processor. This would, for instance, permit running programs with varying capacity. In order to keep as simple as possible not only the actual value determination and the nominal value indication, but also the regulator, a preferred embodiment of the invention provides for a variable gain amplifier which controls the armature excitation current of a single phase or a polyphase generator, with the load being connected to the stator winding. Thereby, it is also advantageous that such a load device is not subject to disturbances.

BRIEF DESCRIPTION OF THE DRAWINGS

In the following, the invention is shown in detail in FIGS. 1 and 2 as block diagrams of two embodiments of the invention.

DETAILED DESCRIPTION OF A PREFERRED EMBODIMENT

Figure 1:
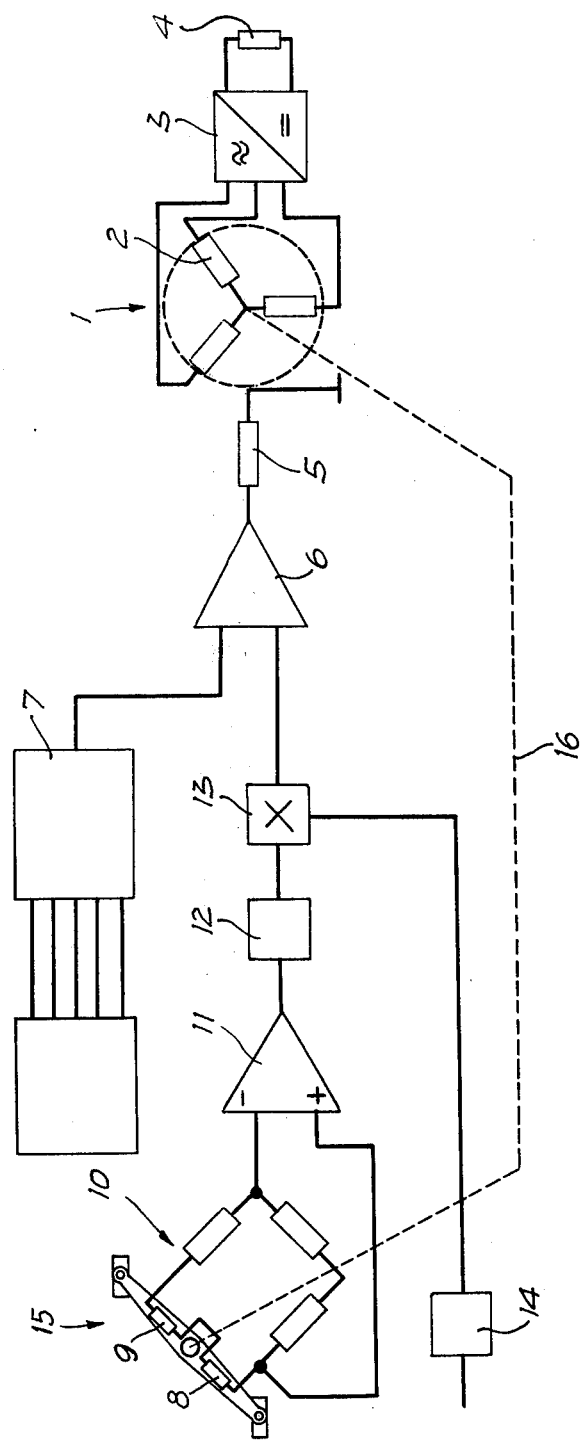

The ergometer of FIG. 1, portions of which are not fully shown, has as the driving machinery, a foot pedal, the revolutions of which are transmitted by a connection 16, such as a drive chain, to the rotor of a three-phase generator 1 of a load device. A load resistor 4 of non-variable size is connected by way of a rectifier 3 to the stator winding 2 of the generator 1. The rotor of the generator 1 carries an exciter coil 5. The brake torque producible by the generator 1 depends on the amount of the exiter current flowing through the exciter coil 5, the brake power of the brake torque and the speed of the rotor. A ventilator or fan, not shown in the drawings, which is connected to the rotor, insures a sufficient cooling of the coils of the generator and of the load resistor 4.

The magnitude of the exciter current flowing through the exciter coil 5 and, therefore, also the magnitude of the brake power of the generator 1, which is transformed into heat losses in the generator and particularly in the load resistor 4, is controlled by a variable gain amplifier 6 on the basis of the preset nominal value and the actual value of the power transmitted by the user to the foot pedals 15. The variable gain amplifier 6 compares the actual value with the nominal value and controls the exciter current continuously in such a way that the deviation is as small as possible. The nominal value is prescribed for the variable gain amplifier 6 by a digital-to-analog converter 7, the inputs to which are connected to a processor which calculates the nominal value on the basis of data which, for instance, can be entered via keys or on the basis of given and/or stored data.

The variable gain amplifier 6 has, in addition to the nominal value input from digital-to-analog converter 7, an actual value input. To determine the actual value of the driving power produced by the user with the foot pedals 15, a wire strain gauge 8 is attached to an element which undergoes a deformation proportional to the torque. For instance, the gauge 8 is attached to a supporting component of the gearing which deforms in accordance with a force transmitted by a drive chain between the foot pedals 15 and the generator 1, or to one arm of the foot pedals 15 in such a way that it measures the deformation of the component, which is effected by the force applied on the component by the user. On the basis of the bending or deformation as determined by the wire strain gauge 8, the transmitted torque can be determined. If the wire strain gauge 8 is attached to one of the arms of the foot pedals 15, then a wire strain gauge 9, connected in series with gauge 8, is correspondingly attached to the other arm, therefore, permits a determination of the torque applied by the user on the driving machinery via the other arm of the foot pedals 15. The wire strain gauge 8, and, if used, the second wire strain gauge 9 as well, are located in one of the branches of a strain gauge bridge, identified generally by reference numeral 10, the diagonal voltage of which is applied across the two inputs of a sum-and-difference amplifier 11. To the output of the amplifier 11, there is connected an integrator 12, which integrates the torque over each revolution of the foot pedals 15.

The output of the integrator 12 is connected to one of the inputs of a multiplier circuit 13. The other input to the multiplier circuit 13 is connected to a tachometer 14, which measures the rotational speed corresponding to the measured torque, i.e., in the case of a torque measured at the foot pedals 15, the rotational speed of the foot pedal, and transforms it into a respective electrical signal. Since the multiplier circuit 13 forms the product of the torque and of the rotational speed of the foot pedals 15, the output magnitude of the multiplier circuit 13 represents the actual value of the power produced by the user with the foot pedals 15.

To what extent this power is proportioned between electrical losses and mechanical losses is irrelevant, since the variable gain amplifier controls the generator 1 and thereby the electrical losses in such a way that, independently of the rotational speed, the sum of all power losses equals the actual value of the power produced by the user on the foot pedals.

Figure 2:
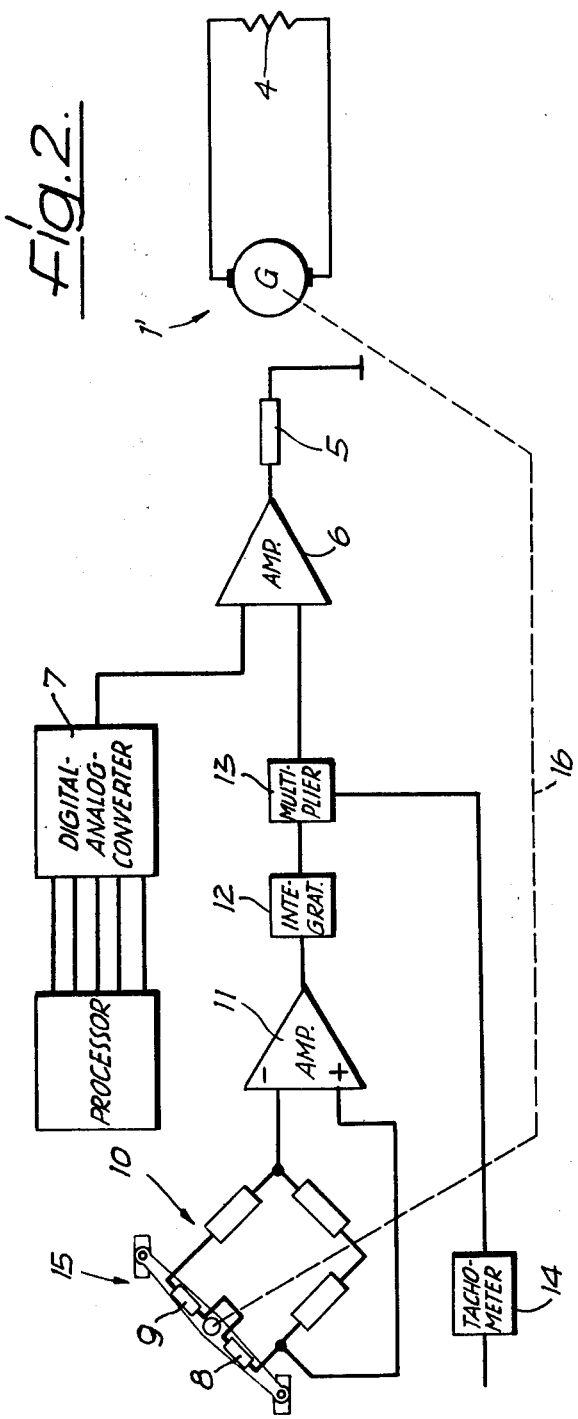

FIG. 2 illustrates a second embodiment of the invention which is substantially identical to the embodiment of FIG. 1 except that a single phase generator 1' is used instead of the three-phase generator 1 of FIG. 1.

Although only a preferred embodiment is specifically illustrated and described herein, it will be appreciated that many modifications and variations of the present invention are possible in light of the above teachings and within the purview of the appended claims without departing from the spirit and intended scope of the invention.

What is claimed is:

1. In an ergometer having a driving machine, said machine including drive means for producing a rotational movement, said drive means including a rotatable drive shaft and force application means connected to said shaft and adapted to be directly engaged by a user for setting said drive means in rotational motion, a load device comprising a generator connected to the driving machine, a load connected to the output of the generator and a regulator controlling the electrical power dissipation of the load device on the basis of a comparison between a given nominal value produced by a nominal value transmitter and an actual value produced by an actual value transmitter, the improvement wherein said actual value transmitter comprises a first measurement transducer means directly coupled to said force application means of said drive means for determining the torque exerted by the user on said force application means of said drive means and for converting the measured torque into a first electrical signal, a second measurement transducer means for determining the speed of a component upon which the measured torque is applied and for converting the speed into a second electrical signal, and a multiplier means connected to said first and second measurement transducer means for forming the product of said first and second electrical signals representing the actual value of the power transmitted to said force application means by the user.

2. The improvement according to claim 1, including integrator means connected between said first measurement transducer means and said multiplier means.

3. The improvement according to claim 1, wherein said first measurement transducer means comprises a strain gauge bridge having an output connected to a sum-and-difference amplifier.

4. The improvement according to claim 3, wherein said strain gauge bridge includes a wire strain gauge operatively connected to a rigid component said force application means of said drive means which deforms elastically in accordance with the torque to be measured.

5. The improvement according to claim 1, wherein said nominal value transmitter comprises a digital-to-analog converter connected to a processor.

6. The improvement according to claim 1, wherein said generator includes an armature excitation coil and a stator winding and a variable gain amplifier connected to said armature excitation current, said load being connected to the stator winding of the generator.

7. The improvement according to claim 6, wherein said generator is a single phase generator.

8. The improvement according to claim 6, wherein said generator is a polyphase generator.

9. The improvement according to claim 1, wherein said force application means comprises foot pedals having arms, said first measurement transducer means being operatively connected to at least one of said arms.

10. The improvement according to claim 9, wherein said first measurement transducer means comprises a strain gauge operatively connected to said one foot pedal arm, said foot pedals being drivingly connected to said generator by a drive chain.

11. The improvement according to claim 9, wherein said first measurement transducer means comprises a strain gauge operatively connected to each arm of said foot pedals, and electrically connected in series in a strain gauge bridge.

* * * * *